United States Patent [19]

Parsons et al.

[11] Patent Number: 5,545,229

[45] Date of Patent: Aug. 13, 1996

[54] FUNCTIONAL AND BIOCOMPATIBLE INTERVERTEBRAL DISC SPACER CONTAINING ELASTOMERIC MATERIAL OF VARYING HARDNESS

[75] Inventors: John R. Parsons, Perth Amboy; Casey K. Lee, Short Hills; Noshir A. Langrana, Robbinsville, all of N.J.; Alastair J. Clemow, North Smithfield, R.I.; Elizabeth H. Chen, Sharon, Mass.; Monica V. Hawkins, Parsippany, N.J.

[73] Assignees: University of Medicine and Dentistry of NJ, Newark; Rutgers University, Piscataway, both of N.J.

[21] Appl. No.: 98,698

[22] Filed: Jul. 28, 1993

Related U.S. Application Data

[63] Continuation of Ser. No. 832,364, Feb. 7, 1992, abandoned, which is a continuation-in-part of Ser. No. 776,708, Oct. 9, 1991, Pat. No. 5,171,281, which is a continuation of Ser. No. 382,207, Jul. 24, 1989, abandoned, which is a continuation-in-part of Ser. No. 233,617, Aug. 18, 1988, abandoned.

[51] Int. Cl.⁶ ..................................................... A61F 2/44
[52] U.S. Cl. ............................................................. 623/17
[58] Field of Search ................................. 623/17, 16, 11, 623/18, 20; 606/61, 62, 63, 64

[56] References Cited

U.S. PATENT DOCUMENTS

| | | |
|---|---|---|
| 3,503,189 | 3/1970 | Nesbitt-Dufort . |
| 3,593,342 | 7/1971 | Niebauer et al. . |
| 3,683,422 | 8/1972 | Stemmer et al. . |
| 3,687,728 | 2/1975 | Stubstad et al. . |
| 3,867,728 | 2/1975 | Stubstad et al. ................... 623/17 |
| 4,146,936 | 4/1979 | Aoyagi et al. . |
| 4,202,055 | 5/1980 | Reiner et al. . |
| 4,222,128 | 9/1980 | Tomonaga et al. . |
| 4,309,777 | 1/1982 | Patil . |
| 4,313,232 | 2/1982 | Habal et al. . |
| 4,314,380 | 2/1982 | Miyata et al. . |
| 4,349,921 | 9/1982 | Kuntz . |
| 4,356,571 | 11/1982 | Esper et al. . |
| 4,366,183 | 12/1982 | Ghommidh et al. . |
| 4,454,612 | 6/1984 | McDaniel et al. . |
| 4,512,038 | 4/1985 | Alexander et al. . |
| 4,576,608 | 3/1986 | Homsy . |
| 4,599,085 | 7/1986 | Riess et al. . |
| 4,636,217 | 1/1987 | Ogilvie et al. . |
| 4,655,777 | 4/1987 | Dunn et al. . |
| 4,662,888 | 5/1987 | Field . |
| 4,711,286 | 12/1987 | Kabe et al. . |
| 4,714,467 | 12/1987 | Lechner et al. . |
| 4,911,718 | 3/1990 | Lee et al. . |
| 4,932,969 | 6/1990 | Frey et al. . |
| 5,171,281 | 12/1992 | Parsons et al. ................... 623/17 |
| 5,236,460 | 8/1993 | Barber ................................. 623/17 |
| 5,306,307 | 4/1994 | Senter et al. ....................... 623/17 |
| 5,306,308 | 4/1994 | Gross et al. ....................... 623/17 |

FOREIGN PATENT DOCUMENTS

| | | | |
|---|---|---|---|
| 0317972 | 5/1989 | European Pat. Off. ................. 623/17 |
| 0392076 | 10/1990 | European Pat. Off. ................. 623/17 |
| 3002298 | 7/1981 | Germany ................................. 623/17 |
| 9105521 | 5/1991 | WIPO ..................................... 623/17 |
| 9310725 | 6/1993 | WIPO ..................................... 623/17 |

OTHER PUBLICATIONS

Urbaniak, et al., *J. Biomed. Mat. Res. Symposium*, 4:165–186 (1973).

Product Literature Lin Intervertebral Endprostheis SB Charite.

*Primary Examiner*—Debra S. Brittingham
*Attorney, Agent, or Firm*—Klauber & Jackson

[57] ABSTRACT

The construction and manufacturing technique for a functional biocompatible intervertebral disc spacer is described. This device is useful for a replacement for a degenerated disc in certain treatments of back pain and spinal disease. The disc spacer possesses mechanical properties akin to those of the normal disc and will preserve normal functions of the spinal motion segment. The device achieves the desired properties by varying the hardness of the elastomeric material in its nucleus and annulus.

6 Claims, 9 Drawing Sheets

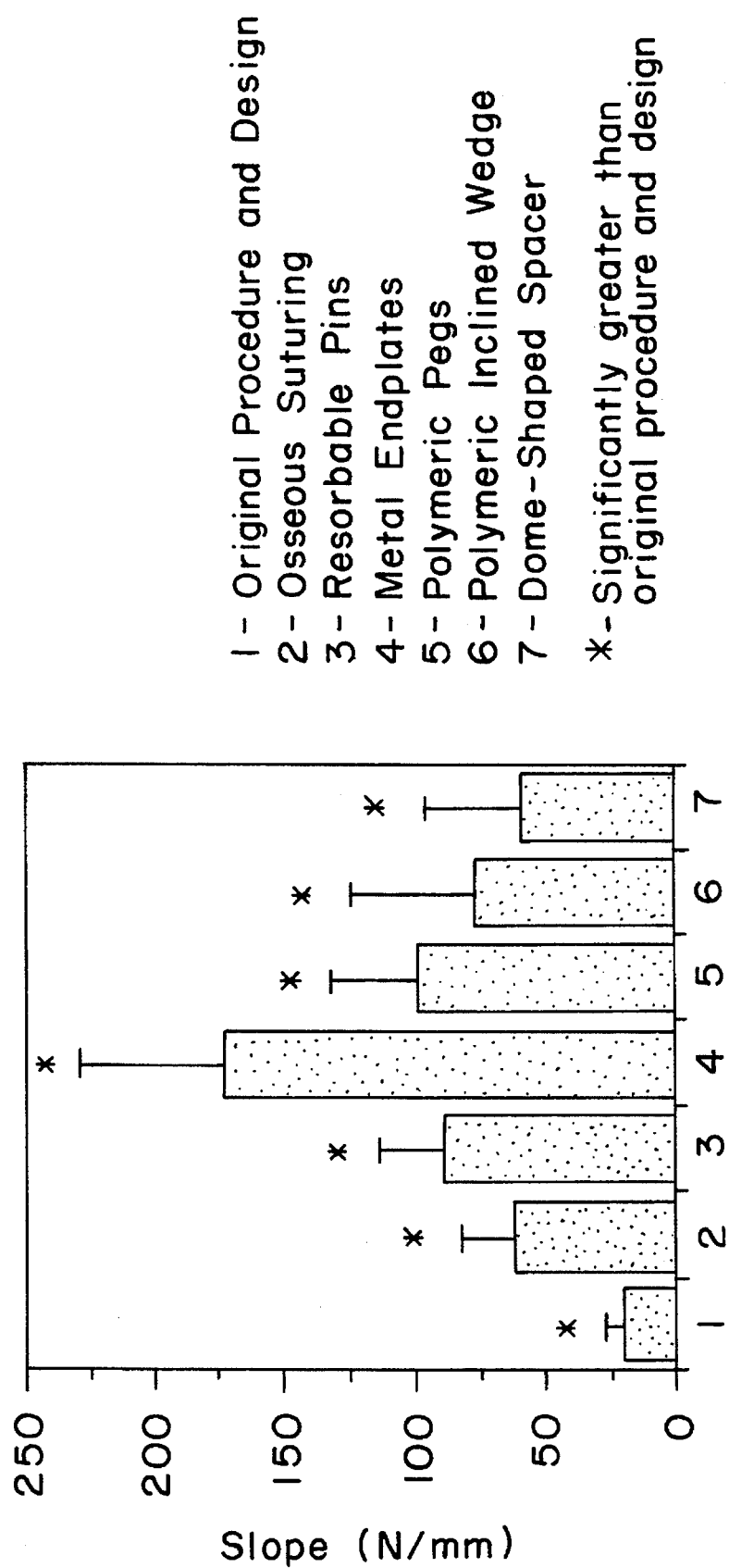

FUNCTIONAL AND BIOCOMPATIBLE INTERVERTEBRAL DISC SPACER CONTAINING ELASTOMERIC MATERIAL OF VARYING HARDNESS

BACKGROUND OF THE INVENTION

This Application is a continuation of U.S. application Ser. No. 07/832,364 a continuation-in-part of U.S. application Ser. No. 776,708 filed on Oct. 9, 1991, now U.S. Pat. No. 5,171,281; which was a continuation of U.S. application Ser. No. 07/382,207 filed on Jul. 24, 1989, now abandoned which is a continuation-in-part of application Ser. No. 07/233,617, filed Aug. 18, 1988, now abandoned priority of which is claimed hereunder.

The intervertebral disc is a complex joint anatomically and functionally. It is composed of three component structures: the nucleus pulposus, the annulus fibrosus and the vertebral endplates. The biomedical composition and anatomical arrangements within these component structures are related to the biomechanical function of the disc.

The nucleus pulposus occupies about 25–40% of the total disc cross-sectional area. It is composed mainly of mucoid material containing mainly proteoglycans with a small amount of collagen. Due to these constituents, the nucleus pulposus has the capacity to bind water and usually contains 70–90% water by weight. Because of this high water content, the nucleus may be mechanically described as an incompressible hydrostatic material. The disc is under constant compressive forces even when the spine is not weight bearing as a result of the tension applied by the annulus fibrosus and the intervertebral ligaments.

The annulus fibrosus is a concentrically laminated structure which contains highly aligned collagen fibers and fibrocartilage embedded in amorphous ground substance. The annular layers are oriented at $\pm 30$ degrees to the longitudinal axis of the spine. In the inner laminae, these annular layers are anchored to the cartilaginous endplate while the outermost layer is attached directly into the osseous tissue of the vertebral body. Usually, the annulus fibrosus has approximately 8–12 layers and has an anterior portion which is about 1.2–1.5 times thicker than its posterior region. Mechanically, the annulus fibrosus is the main stabilizing structure which resists torsional and bending forces applied to the disc. A normal isolated disc provides approximately 35% of the torsional rigidity of a whole intervertebral joint.

The two vertebral endplates are composed of hyaline cartilage and separate the disc from the adjacent vertebral bodies. This layer acts as a transitional zone between the hard, bony vertebral bodies and the softer disc.

The spinal disc may be displaced or damaged due to trauma or a disease process. If this occurs, the nucleus pulposus may herniate and protrude into the vertebral canal or intervertebral foramen, in which case, it is known as a herniated or "slipped" disc. This disc may in turn press upon the spinal nerve that exits the vertebral canal through the partially obstructed foramen, causing pain or paralysis in the area of its distribution. The most frequent site of occurrence of a herniated disc is in the lower lumbar region. A disc herniation in this area often involves the inferior extremities by compressing the sciatic nerve. To alleviate this condition, it may be necessary to remove the involved disc surgically and fuse the two adjacent vertebrae. A number of procedures have been identified and are described in the orthopaedic literature. One such is described in "Orthopedics-Principles and Their Application" Samuel L. Turek, M. D., Lippincott Company, Third Edition, pp. 761–763. In this procedure, a hole is drilled in the spinal column straddling the damaged disc space and the two adjacent vertebral bodies. The hole is then filled with a cylindrical plug or dowel in order to fuse the vertebrae together. The fusion procedure is an excellent method of eliminating symptoms and yet maintaining joint stability, but at the expense of total loss of motion of the fused vertebral joint and increased stress in the juxta or adjacent segments. The adjacent discs will have increased motion and stress due to the increased stiffness of the fused segment. In the long term, this change in the mechanics of the motion of the spine causes these adjacent discs to degenerate. Obviously, a more desirable situation would involve replacing the damaged disc with a suitable biofunctional equivalent so as to return the patient's spine to normalcy. Heretofore, the development of a prosthetic joint device to replace the injured intervertebral disc has been unsuccessful due to the complexity of the structure and biomechanics of the normal disc. About 200,000 disc excision surgeries are performed in the United States each year.

Other spacers for spinal repair have been developed; see for instance those of U.S. Pat. No. 3,867,728, U.S. Pat. No. 4,309,777, U.S. Pat. No. 4,349,921, U.S. Pat. No. 4,553,273 and U.S. Pat. No. 4,714,469. None of these, however, have been commercially developed. The prostheses of U.S. Pat. Nos. 4,349,921, 4,553,273 and 4,714,469 are essentially rigid bodies which serve to stabilize the spine but do not allow motion within the disc itself. U.S. Pat. No. 4,309,777 consists of a disc which allows motion, but this is achieved by the use of springs contained within the body of the disc. This system suffers from the disadvantage of extreme complexity and doubtful long-term survival. U.S. Pat. No. 3,867,728 by Stubstad, et al. discloses a device which replaces the natural disc with one of similar shape and strength. The disc may be constructed from an elastic polymer such as silicone and reinforced with fabric. The top and bottom surfaces may be provided with an open pored material such as a velour to encourage tissue ingrowth. The purpose of this invention is to provide a system capable of withstanding the loads imposed upon it during normal human activities. As a result, the preferred construction of the disc provides for reinforcement against only compressional loads.

In practice, the spine is subjected to both compressional and torsional loading and, to be successful, any device must be capable of withstanding both forms. In addition to strength, any prosthetic disc must deform elastically in a similar manner to the natural structure in order that normal stresses are induced within the adjacent vertebral bodies. If too stiff a structure is used, then the disc will deform too little, and the natural discs both superior and inferior to the prosthetic device will be required to deform excessively. This is a similar situation to that which occurs when bony fusion across the disc is employed.

If, on the other hand, the device possesses too little stiffness, either in compression or torsion, then excessive motion will occur, the device will bulge out and pain may result. This is an equivalent situation to a failed bony fusion. U.S. Pat. No. 3,867,728 describes a device which is concerned only with the ultimate strength and not with any elastic properties. Therefore, the reinforcement of the elastomer through a fabric layer results only in an increase in compressional strength and fails to address the equally important problem of elasticity in compression and torsion. The fabric disclosed by U.S. Pat. No. 3,867,728 does not possess the necessary correct construction to provide the desired functional characteristics. As a result, the prosthesis of U.S. Pat. No. 3,867,728 fails to satisfy functional criteria for a replacement disc.

OBJECTS OF THE INVENTION

It is the object of the present invention to provide a novel intervertebral disc spacer which can be used to replace a damaged or diseased disc with a device that is chemically, geometrically and mechanically biocompatible and can be used to replace the natural structure.

It is another object of the present invention to provide an intervertebral disc spacer which utilizes a pair of endplates that are effective for impeding dislodgement of the device during torsional or compressive strain.

It is a further object of this invention to provide a novel method of manufacturing a functional and biocompatible intervertebral disc spacer having similar or equivalent biomechanical properties to those of a normal disc.

It is a still further object of the present invention to provide a novel method of alleviating the pain and/or paralysis of a damaged or diseased disc which comprises replacing the damaged or diseased disc with a functional and biocompatible intervertebral disc spacer.

SUMMARY OF THE INVENTION

The present invention relates to a novel functional and biocompatible intervertebral disc spacer, its method of manufacture, and methods of use therefor. More particularly, the present invention concerns a functional and biocompatible intervertebral disc spacer having biomechanical properties similar or equivalent to those of a normal disc.

Additionally, the present invention encompasses improvements in endplate design which are useful for impeding dislodgement of the prosthetic device due to shear forces which may be realized after the device is implanted.

DETAILED DESCRIPTION OF THE INVENTION

Figure 1:
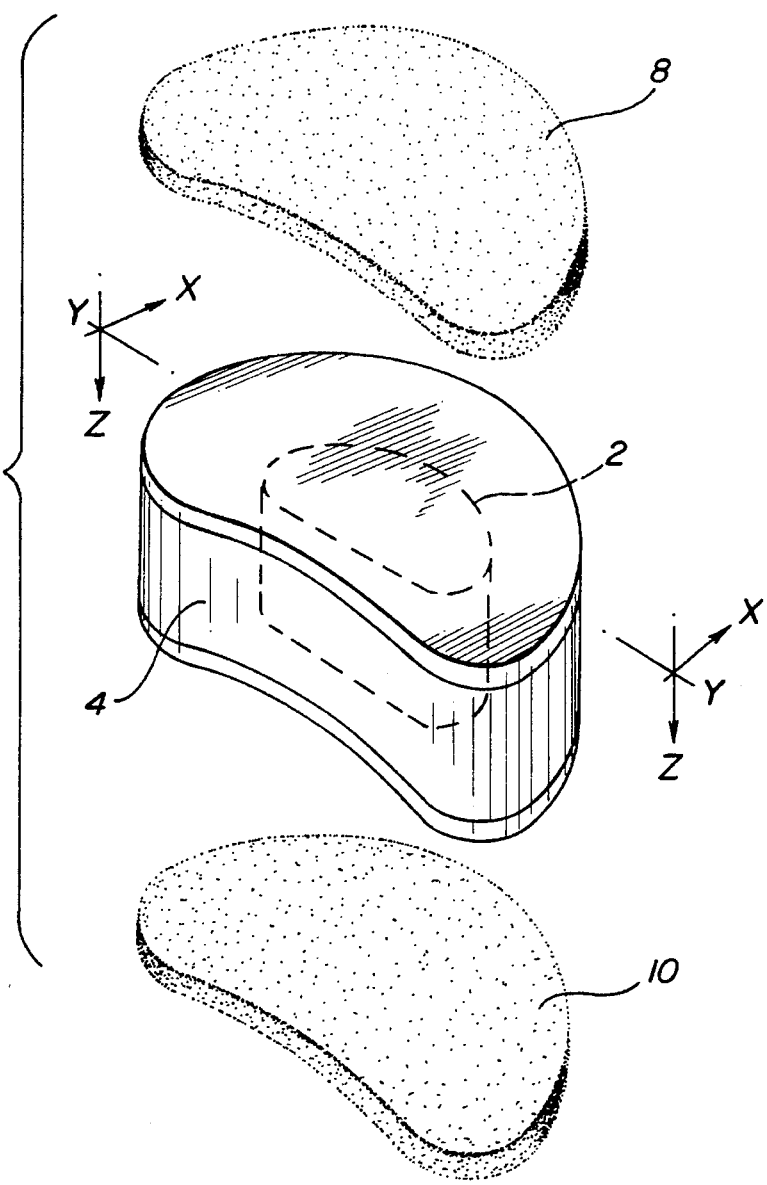
FIG. 1 is a view in perspective of a spinal disc spacer manufactured according to the present invention.
Figure 2:
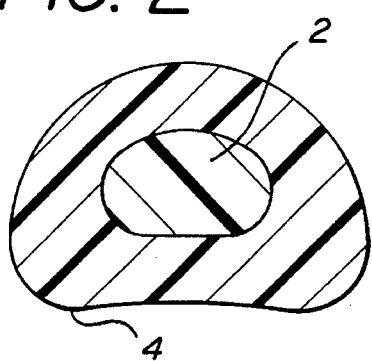
FIG. 2 is a top view of a spinal disc spacer manufactured according to the present invention.
Figure 3:
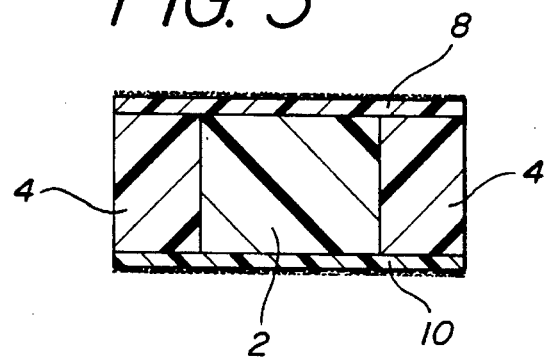
FIG. 3 is a cross-section view through the center of a spinal disc spacer manufactured according to the present invention.

The functional and biocompatible intervertebral spacer of the present invention comprises a central core 2 of a soft biocompatible elastomer shaped and sized so as to approximate the shape and size of a nucleus pulposus of a natural intervertebral disc; an outer ring 4 of stiffer elastomeric material surrounding said central core to approximate the size and shape of a natural annulus fibrosus; and endplates 8 and 10 comprised of a suitably stiff biocompatible material and affixed, one to each end, to the outer ring/central core. In a preferred embodiment, the core 2 will consist of 20–50% of the area of the spacer, and the outer ring 4 will consist of 50–80% of the area of the spacer. The relative size of the central core and the thickness of the outer ring in the radial direction, as well as the selection of material hardness, can be varied in order to more finely match the mechanical properties of the composite prosthesis to that of the normal disc.

The elastomeric material utilized in the core 2 and outer ring 4 is any appropriate biocompatible thermoplastic material. The hardness of the material for each component part of the prosthesis is chosen so that the composite prosthesis will reproduce the mechanical properties of the natural disc it is designed to replace. Preferably, the elastomeric material or materials utilized for the core 2 will have a hardness in the range of 20–70 shore-A. The elastomeric material or materials utilized for the outer ring 4 will preferably have hardnesses in the range of 40–80 shore-A. The outer ring 4 may be composed of one or as many as five layers of elastomers of varying hardness. Preferably, however, the outer ring 4 contains one or three layers of elastomers of varying hardness. The central core 2 may likewise contain 1–5 layers of elastomers of varying hardness, but 1–2 layers are preferred.

The biocompatible elastomeric material utilized in the present invention may be any suitable thermoplastic elastomeric material. Suitable thermoplastic elastomers are those commercially available under the trademark C-Flex® (Concept, Inc.) or Pellethane® (Dow Chemical). A preferred thermoplastic elastomer for use in the present invention is a biocompatible polysiloxane modified styrene-ethylene/butylene (SEBS) block copolymer sold by Concept Polymer Technologies, Inc., Clearwater, Fla. under the C-Flex® trademark. These elastomers are available or can be formulated so as to form final products of varying stiffness. Although the present invention preferably utilizes the same elastomeric material in various degrees of stiffness for the various components of its disc spacer, it may also utilize different elastomeric materials for the various parts and various layers thereof.

In highly preferred embodiments of the present invention, the elastomeric material, relative areas and number of layers are chosen so as to afford a spacer having a mean axial stiffness of 1000–3500 newtons/mm and a mean torsional stiffness of 0.8–3.0 Nm/degree. Most preferably, a spacer will possess a mean axial stiffness of 2000–3000 newtons/mm and a mean torsional stiffness of 1–2 Nm/degree. These criteria afford a spacer with properties close to that of the human lumbar disc.

The endplates 8 and 10 for use in the spacer of the present invention can be manufactured from a variety of suitably stiff biocompatible materials; including more rigid elastomers of the same type as used in the disc itself. The suitably stiff endplate material must be relatively rigid and able to endure the biomechanical stresses placed upon it in the joint. Typically, the endplates are formed from rigid substances such as a biocompatible metal, for instance, precut titanium discs, and/or formed in a mold from biocompatible thermoplastic or thermoset resins, such as a polyurethane elastomer having a hardness of about 90–100 shore-A.

The endplates may also incorporate a mechanism for attachment to adjacent bony vertebral bodies. Such mechanisms include, but are not limited to, mechanical interlock, frictional fit, ingrowth into a porous structure such as a porous sintered surface, hydroxyapatite coatings or cementing agents such as polymethyl methylacrylate "bone cement".

The method of manufacture of the spacer of the present invention involves injection, transfer or compression molding of the core and outer wrapping.

Typical molding or casting techniques can be used to form polymer endplates. Metallurgical techniques can be used to form metal endplates. Both metal endplates and polymer endplates may have porous surfaces or hydroxyapatite surfaces to aid in attachment to adjacent bony vertebral bodies. These surfaces may be porous metallic or polymeric sintered surfaces, and would be used with bone cement.

The assembly of the spacer typically begins with the formation of a suitably shaped and sized core formed of the elastomer material. A pre-set amount of the powdered elastomer is compacted into a female mold of appropriate cross section and thickness. The filled mold with the male portion inserted is placed between thermal platens within a compression ram and then compressed. The pressure is then reduced. The temperature is increased until the melt temperature of the material is reached. The core may be held at an elevated temperature to facilitate bonding. This melt temperature is dependent upon the hardness and type of the chosen elastomeric material. The part is cooled to room temperature, and the nucleus is unmolded and any flash removed.

Next, the outer ring (annulus) is molded. The premolded nucleus is secured to the center of the bottom of the annular mold with a drop of adhesive. A pre-set amount of annular material, depending on the size of the annulus, is compacted by hand around the nucleus. Again, the male portion of the mold is positioned, and the pressure raised to approximately 1000 lbs. and then reduced and held at approximately 500 lbs. The temperature is then elevated to the temperature of the melting point of the annular material. The part may be held at an elevated temperature to facilitate bonding. The part is then cooled to room temperature, decompressed, unmolded and removed of any flash. If the outer ring (annulus) consists of more than one layer of elastomer, the varying layers of elastomers are molded to the core in a stepwise fashion, working from the core to the outer edge of the spacer.

The endplates 8 and 10 may be applied with additional elastomer to the top and bottom of the annulus/nucleus assembly. Alternatively, a pre-set amount of elastomeric endplate material can be placed on the bottom surface of the appropriate mold in a uniform layer. The annulus/nucleus is placed on top of the endplate material. Another uniform layer of material is placed on the top and compacted to form the second endplate. The male mold is positioned and the pressure and temperature cycles similar to that used for the previous molding steps is performed with the mold temperature raised to the temperature of the melting point of the endplate material. The part may be held at an elevated temperature to facilitate bonding. This type of assembly results in molded endplates.

Lastly, a porous layer of either hydroxylapatite or polymeric material can optionally be added to the outer surfaces of the endplates. The hydroxylapatite may be attached to the endplates by spreading a uniform layer of hydroxylapatite particles on a heated surface. The temperature of the particles is raised to the melt temperature of the endplate material and the flat surface of each endplate is pressed into the heated hydroxylapatite. A porous polymeric surface can be achieved by a process of sintering polymeric particulate to the surface or by including particles in the surface which are later dissolved in a separate process leaving behind controlled porosity.

Additionally, the endplates can be molded so as to provide for a mechanical interlock with the adjacent bone surface. They may also be subsequently "roughened" so as to provide a surface appropriate for attachment to the adjacent bones with polymethyl methacrylate bone cement.

Typically, molds are utilized to manufacture spacers having a geometry consistent with that of a natural disc. Although the disc size can, of course, be varied, a suitable size for the spacer is one having a cross section area of 1100 mm$^2$ major diameter of 44 mm and a minor diameter of 30 mm.

The present invention contemplates manufacture of the spacers in a variety of sizes since one size is not suitable for all people or all locations within the spine. Additionally, the spacer of the present invention can be sized so that its total diameter is smaller than that of a natural disc, i.e. a size which approximates 30–80% of the diameter of the natural disc. This size of spacer can then be utilized in cases where only a central part of the natural disc is removed and replaced. In such cases, the damaged or diseased central portion is replaced by a spacer of approximately the same size as the portion removed. This type of replacement is particularly advantageous since the healthy portion of a patient's disc is retained. Obviously, molds can be developed for the various sizes necessary, and it is envisioned that the disc spacer of this invention will be manufactured in a variety of sizes so as to make the necessary selection available to the treating physician.

One important design consideration for a synthetic vertebral spacer is stabilization of the device which can be affected by the vertebral endplates. Post-surgical migration of the implant can be minimized.

Hydroxyapatite (HA) can be embedded or deposited onto the flat cranial and caudal surfaces of the implant and used to encourage bone ingrowth and long-term stability of the implant. However, a fibrous tissue layer may form between the implant and the adjacent vertebral body, with or without bony apposition. Early migration of the spacer is observed in nearly half of all test animals, and it is clear that rigid immediate fixation is not readily achieved. Even in those implants which did not migrate, a fibrous tissue layer was observed.

Post-operative implant migration was identified as a crucial problem by animal studies. Such migration resulted in the formation of osteophytes and contributed to a lack of bony ingrowth. The animals used in the studies described herein were not restrained post-operatively and many were noted to be extremely active, jumping and wagging their tails within several days. Under such forces, a sutured annulus may be unable to adequately hold the spacer in place until the remaining annular layers heal.

Numerous designs and surgical modifications were studied in "push out" experiments to evaluate their ability to resist shear forces on the spinal implant.

Surgical procedures effectively "close off" the surgical insertion portal in the annulus improved initial stability, but did not prevent implant migration in all instances. Restraining pins as well as endplate design modifications added significantly to the initial shear stability at the bone-implant interface. Restraining used above provided no additional shear stability, and represented an additional material which may evoke an inflammatory response. The use of endplate design modifications was therefore deemed much more favorable.

Endplate design modifications were tested, including pegs, inclined planes, and domes molded onto the endplates which interdigitate with the adjacent bone of the vertebrae improved the stability of the implant. In animal models, e.g., canine, it is unlikely that the multiple small pegs placed on the endplates were spaced far enough apart to act independently since the area of the canine implant is only 110 mm$^2$. However, on a human scale, the area of the implant is about 730 mm$^2$. On this larger scale, independence exists between the small pegs, and three smaller pegs may provide significant and unexpected shear stability, in contrast to a single, large inclined plane.

However, during evaluation using the canine model, it was noted that the pegs were sheared off several times during implantation, and other times during the "push out test". In addition to loss of mechanical fixation, this presents the additional problem of creating loose particulate material as well as damage to the surface of the implant. No such complications were presented by the dome-shaped spacers which demonstrated the greatest resistance to lateral shear. This resistance was the result of fitting of the dome-shaped (convex) implant into the concave defect which was surgically created.

An initial 3-month study with this new design indicated no implant migration, and only minimal scar and/or osteophyte formation.

The following examples, and in particular, Examples 1 and 2, illustrate the preparation and mechanical testing of disc prostheses of the present invention. Example 3 presents in vivo analysis of a prosthesis prepared with a hydroxylapatite coating thereon.

EXAMPLE 1

The assembly of the spacer begins with the formation of a suitably shaped and sized core formed of the elastomer material. A pre-set amount of the powdered elastomer is compacted into a female mold of appropriate cross section and thickness. The filled mold with the male portion inserted is placed between thermal platens within a compression ram. The mold is first compressed with an approximately 1000 lb. load. The pressure is then reduced and held at approximately 500 lbs. The temperature is increased at a rate of 5° C. per minute until the melt temperature of the material is reached. The core may be held at an elevated temperature to facilitate bonding. This melt temperature is dependent upon the hardness and type of the chosen elastomeric material. The part is cooled to room temperature, and the nucleus is unmolded and any flash removed.

The outer ring (annulus) is molded next. The premolded nucleus is secured to the center of the bottom of the annular mold with a drop of adhesive. A pre-set amount of annular material, depending on the size of the annulus, is compacted by hand-around the nucleus. Again, the male portion of the mold is positioned, and the pressure raised to approximately 1000 lbs. and then reduced and held at approximately 500 lbs. The temperature is then elevated at 5° C./min. to the temperature of the melting point of the annular material. The part may be held at an elevated temperature to facilitate bonding. The part is then cooled to room temperature, decompressed, unmolded and removed of any flash.

If the endplates are separately manufactured, they are applied with additional elastomer to the top and bottom of the assembled annulus/nucleus. Alternately, the endplates may be directly molded onto the core-outer ring assembly. A pre-set amount of endplate material is placed on the bottom surface of the appropriate mold in a uniform layer. The annulus/nucleus is placed on top of the endplate material. Another uniform layer of material is placed on the top and compacted to form the second endplate. The male mold is positioned and the pressure and temperature cycles similar to that used for the previous molding steps is performed with the mold temperature raised to the temperature of the melting point of the endplate material. The part may be held at an elevated temperature to facilitate bonding.

Lastly, a porous layer of either hydroxylapatite or polymeric material can optionally be added to the outer surfaces of the endplates. The hydroxylapatite may be attached to the endplates by spreading a uniform layer of hydroxylapatite particles on a heated surface. The temperature of the particles is raised to the melt temperature of the endplate material and the flat surface of each endplate is pressed into the heated hydroxylapatite. A porous polymeric surface can be achieved by a process of sintering polymeric particulate to the surface or by including particles in the surface which are later dissolved in a separate process leaving behind controlled porosity.

EXAMPLE 2

Mechanical Testing

Both compression and torsion/compression tests were conducted. Many different compositions of prosthetic discs have been manufactured and mechanically tested. The devices tested in compression were axially loaded at a rate of 200N/min. up to maximum load of 900N. Axial stiffness was measured between loads of 600 and 800N. The torsion/compression tests were conducted with an axial compression load of 800N and torqued at a rate of 2 Nm/s to a maximum rotation of 3 degrees. Torsional stiffness was measured between 1.5 and 2.5 degrees.

Single Component Discs

A series of discs were manufactured from single hardness compositions of C-Flex®. The compressive and torsional properties of these discs are listed in Table I together with data from testing of human normal discs from the L4-L5 level.

TABLE I

Mechanical Properties of Single Component Disc Prostheses

| Disc Material | Mean Axial Stiffness (±SD) (N/mm) | Mean Torsional Stiffness (±SD) (Nm/deg) |
| --- | --- | --- |
| 35A C-Flex ® | 387 (±3) | 0.16 (NA) |
| 50A C-Flex ® | 612 (±44) | 0.39 (NA) |

TABLE I-continued

Mechanical Properties of Single Component Disc Prostheses

| Disc Material | Mean Axial Stiffness (±SD) (N/mm) | Mean Torsional Stiffness (±SD) (Nm/deg) |
| --- | --- | --- |
| 70A C-Flex ® | 1697 (±105) | 0.64 (NA) |
| 90A C-Flex ® | 3937 (±146) | 3.92 (NA) |
| HUMAN | 1328 (±241) | 2.06 (NA) |

NA = Not Available

These data serve to indicate that matching the combination of both compressive and torsional stiffnesses with a single grade of elastomer is not possible. If a hard grade of C-Flex® such as 90A, is used, torsional properties may be matched but an excessively stiff system in compression is produced. Conversely, if a softer elastomer such as 70A is used, then the compressive stiffness is closer to that desired, however, the torsional stiffness is much lower.

Multi-Component Devices

In order to overcome the deficits outlined above, a series of prostheses were manufactured having compositions as listed in Table II. Their resultant compressive and torsional properties are listed in Table III.

TABLE II

Disc Prosthesis Compositions

| Disc Type | Nucleus Material | Nucleus Area | Annulus Material | Endplate Material |
| --- | --- | --- | --- | --- |
| I | 35A C-Flex ® | 43% | 70A C-Flex ® | 90A C-Flex ® |
| II | 50A C-Flex ® | 43% | 70A C-Flex ® | 90A C-Flex ® |
| III | 35A C-Flex ® | 35% | 70A C-Flex ® | 90A C-Flex ® |
| IV | 35A C-Flex ® | 43% | 50A C-Flex ® | 90A C-Flex ® |

TABLE III

Mechanical Properties of Multicomponent Disc Prostheses

| Disc Type | Mean Axial Stiffness (±SD) (N/mm) | Mean Torsional Stiffness (±SD) (Nm/deg) |
| --- | --- | --- |
| I | 1923 (±226) | 1.01 (±.06) |
| II | 2270 (±17) | 1.00 (±.07) |
| III | 2953 (±81) | 1.26 (±.04) |
| IV | 1008 (±55) | 0.40 (±.00) |
| HUMAN | 1328 (±241) | 2.06 (NA) |

NA = Not Available, Human Disc Level: (L4–L5)

Figure 4:
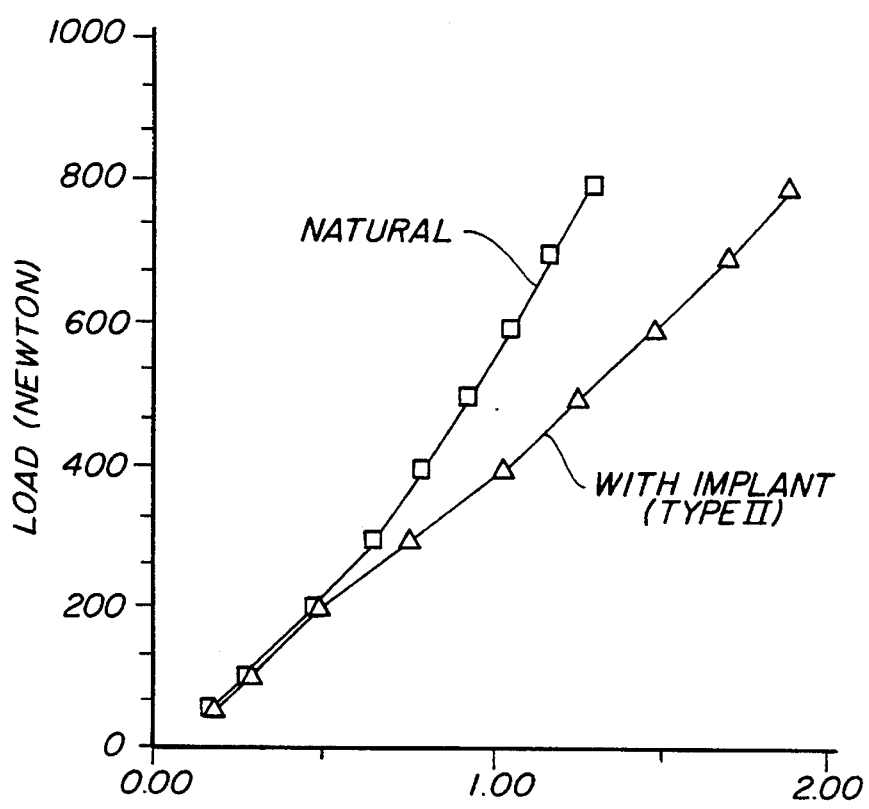
FIG. 4 is a graph showing the results of the mechanical behavior of a disc spacer produced according to the present invention compared to a natural disc in the axial compression test.
Figure 5:
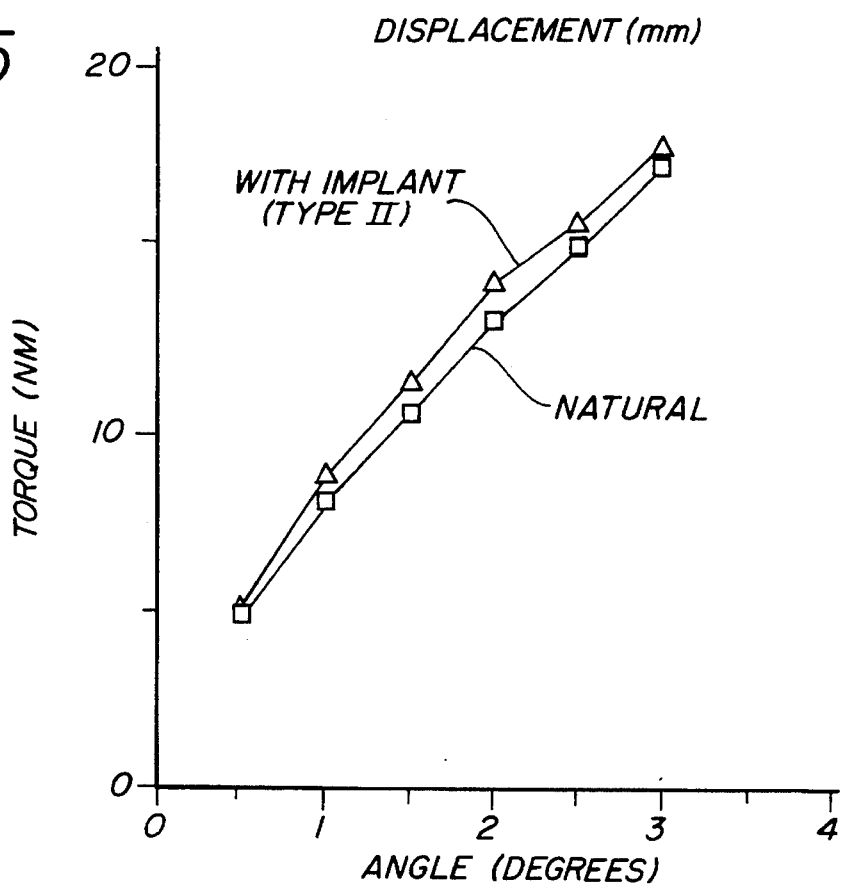
FIG. 5 is a graph showing the results of the mechanical behavior of a disc spacer produced according to the present invention compared to a natural disc in the compression torsion test.

The data show that by changing the various hardnesses and relative sizes of the annulus and nucleus that the mechanical properties of the disc prosthesis may be altered. The size and hardness of the nucleus dominate the properties in axial compression while the size and hardness of the annulus dominate the properties in torsion. In addition, the properties of the human normal disc are within range of the properties attainable with C-Flex® for axial compression. The values for torsion appear low; however, in many cases at least 50% of natural annulus will remain in the patient after prosthetic disc insertion; further, the posterior bony elements of the spine will also remain intact. This remaining tissue will increase the overall in situ torsional properties to a normal level (see below), Mechanical testing was also performed with the prosthesis implanted in the L4/L5 disc space of a functional spinal unit (two vertebral bodies with their common disc). A sample of the data in compression and torsion is shown in FIGS. 4 and 5. Each spinal unit was tested in both uniaxial compression and compression/torsion conditions in the intact state. The compression tests were performed in load control at a constant loading rate of 3.3N/sec. The compression/torsion tests were conducted with the applied compression load held fixed at 800N while the rate of angular deflection was set to 0.1 deg./sec. Then these tests were repeated after the intervertebral disc prosthesis was implanted. Each prosthesis had also been tested alone.

EXAMPLE 3

In Vivo Analysis of Hydroxylapatite Coating

Animal experiments have been performed to demonstrate the benefit of using a porous material such as hydroxylapatite particulate to coat the surface of the endplates to enhance fixation of the prosthesis to bone. Small cylinders of thermoplastic C-Flex® elastomer were manufactured and half were coated with hydroxylapatite in a manner similar to that of the disc prosthesis manufacturing process. These cylinders were implanted in the distal metaphyses of rabbit femora and examined at four and twelve weeks post-operatively. Five animals were utilized for each time period. Each rabbit received a coated sample in one femur while an uncoated sample was placed in the contralateral femur. Mechanical push out tests were performed on four of the five animals in each time period and the remaining animal was used for histological examination.

The results from the mechanical testing revealed significantly higher shear strengths of the hydroxylapatite coated cylinders at both four and twelve weeks, indicating enhanced fixation and attachment over that of the uncoated polymeric cylinders. While the uncoated samples showed no increase in shear stress with time, the coated samples continued to increase in strength from four to twelve weeks. By twelve weeks, the coated implants had shear strengths five times that of the uncoated implants. Histologically, the coated implants revealed good apposition of the coating to the polymeric surface with partial wicking evident around the lateral surfaces of the particles. The hydroxylapatite surface was in intimate contact with trabecular bone with no evidence of fibrous tissue. Bony ingrowth into the interstices of the particulate hydroxylapatite was also observed. The uncoated implants demonstrated a fibrous tissue layer between the polymeric material and bone with a longitudinal orientation of the collagen bundles. No bony contact with the polymer was seen.

The disc spacer of the present invention thus Provides a novel method of alleviating the pain and paralysis of a damaged or disease spine which comprises surgically replacing the damaged or diseased natural disc with one manufactured according to the present invention. Depending upon the patient's age and the position of the diseased or damaged disc, a physician will select a suitably sized replacement disc for insertion between the natural vertebrae.

EXAMPLE 4

Endplate Design Evaluation

Figure 10:
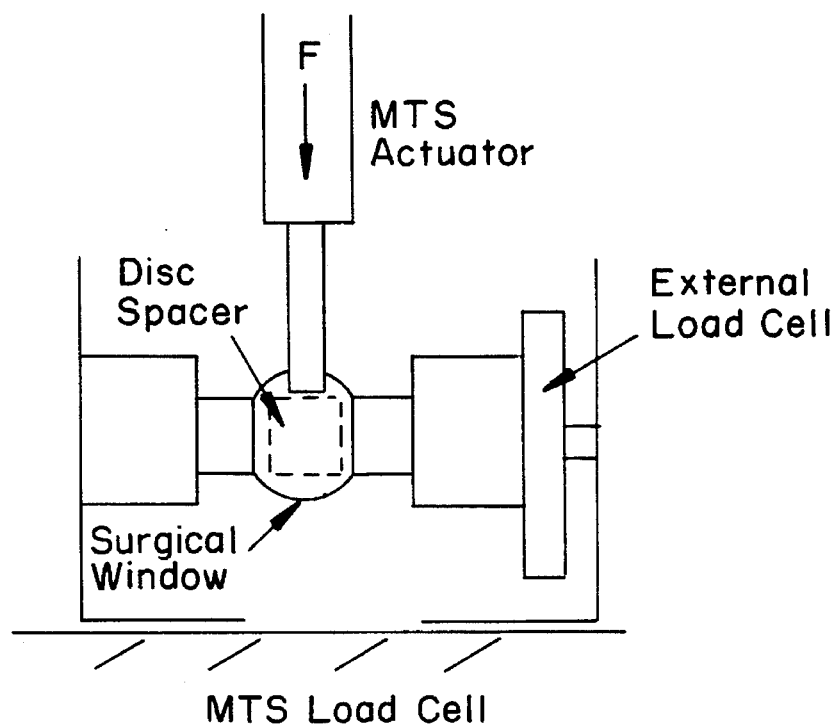
FIG. 10 is a diagram of a Push Out Test Apparatus for Endplate Design Evaluation.

Fourteen canine cadaver lumbar spines were harvested, dissected, and mounted in the manner previously described. A spacer of a given design was then implanted into the L2–3 or L5–6 disc space. The segment and two grips were mounted horizontally in the MTS test frame using a custom jig so that the surgical portal was opposite the point of application of load as shown in FIG. 10. A 100N compressive load was applied axially through the segment and monitored through an external load cell. This axial load mimicked normal compressive loads due to muscle forces.

A space was created in the side of the annulus opposite the surgical window and the actuator was lowered through this space until it contacted the implant. At a constant loading rate of 1N/sec, the load was increased until the implant was dislodged from the segment through the original surgical approach.

Both initial stability and minimal long-term micromotion are required for implant stability. Thus, the force needed to reach 0.3 mm displacement as well as the maximum force needed to dislodge the spacer from the specimen were both measured. Additionally, the slope of the initial portion of the force-displacement graph was calculated in order to evaluate initial resistance to lateral shear.

A baseline was established by using a standard posterolateral surgical approach and a simple non-interlocking implant design. The proximal and distal endplates of the implant were flat, parallel surfaces. Two variations in surgical technique were investigated with this simple implant. The first was the use of osseous sutures which traversed through the proximal vertebral body, the remaining annulus (as close to the implant as possible), and the distal vertebral body. The second technique utilized "resorbable" pins which were placed in a "toed-in" fashion into the proximal and distal vertebral bodies to restrain lateral movement of the implant. Polysulfone pins 3.25 mm in diameter and 10 mm in length were used for testing since the mechanical properties of polysulfone are similar to polylactic acid (PLA) and polyglycolic acid (PGA). Both PLA and PGA are resorbable materials that have been used for fracture fixation.

Figure 6A:
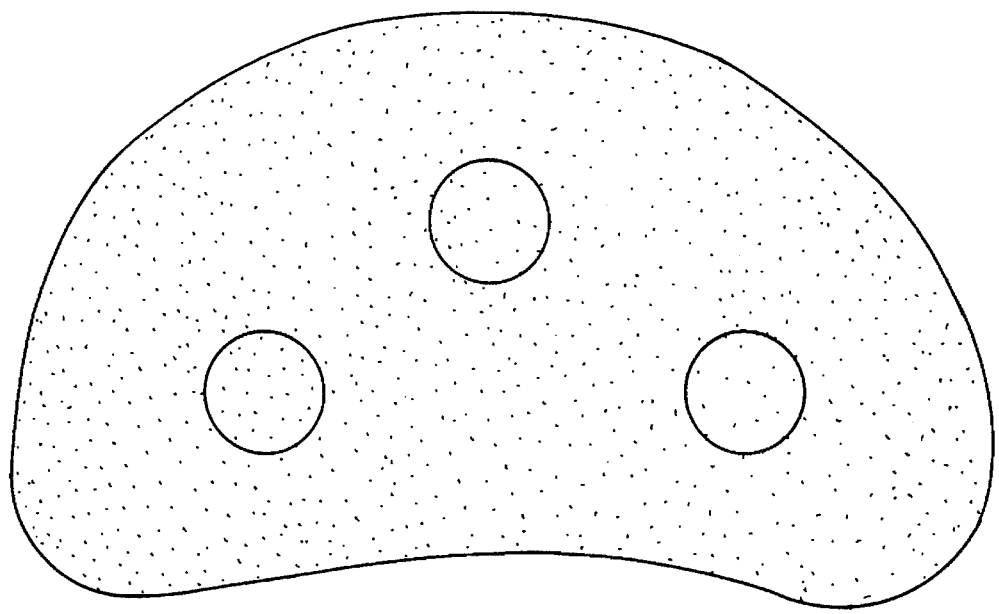
FIG. 6 is a side view in cross-section of a spinal disc spacer with a plurality of metal spikes on the outer surface of the endplates.
Figure 6B:
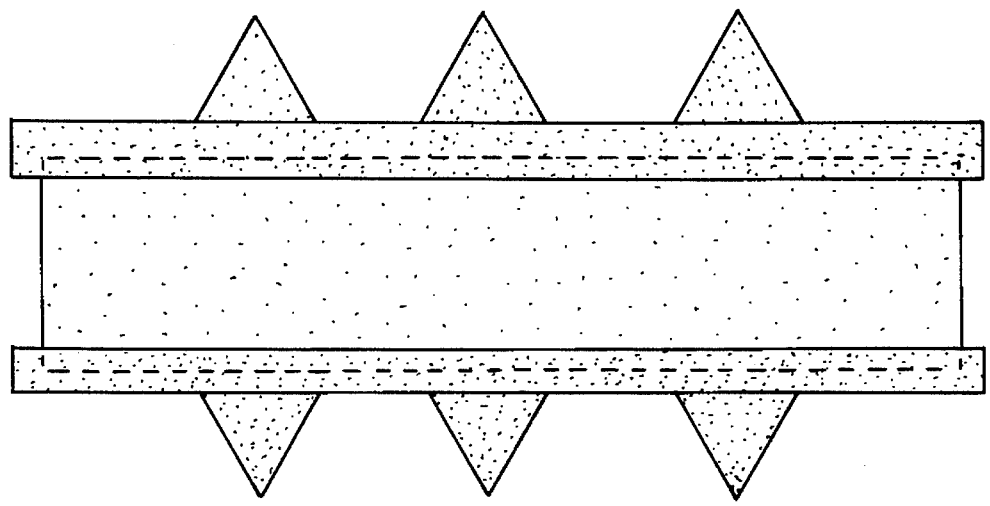

Spiked metal endplates were also included for comparison purposes. As can be seen in FIG. 6, a spacer with flat parallel surfaces was placed between two cupped metal endplates each with three 1.5 mm cone-shaped spikes.

Figure 7A:
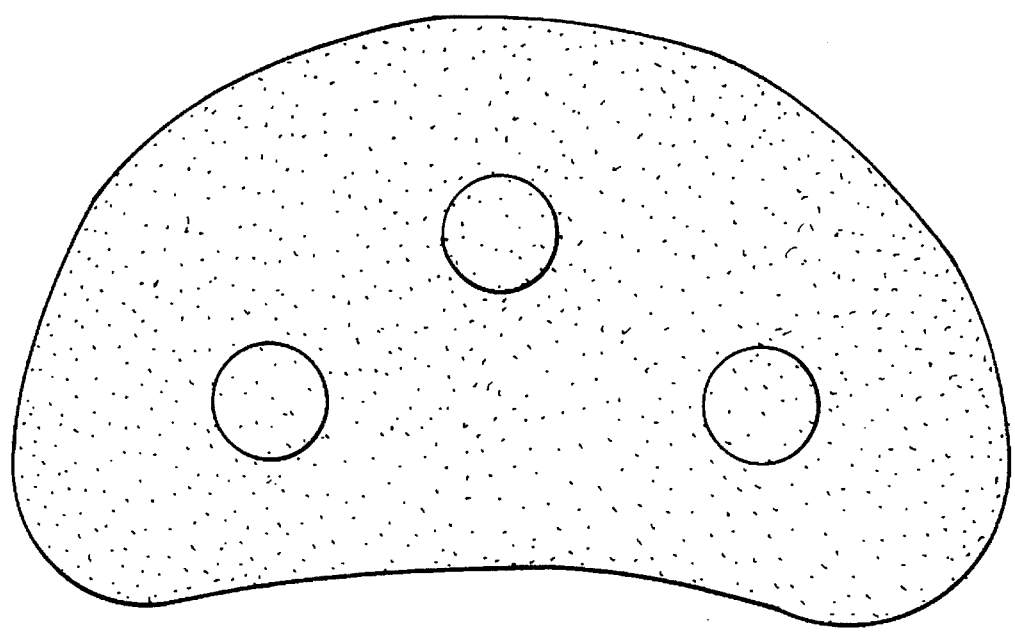
FIG. 7 is a side view in cross-section of a spinal disc spacer with a plurality of molded pegs on the outer surfaces of the endplates.
Figure 7B:
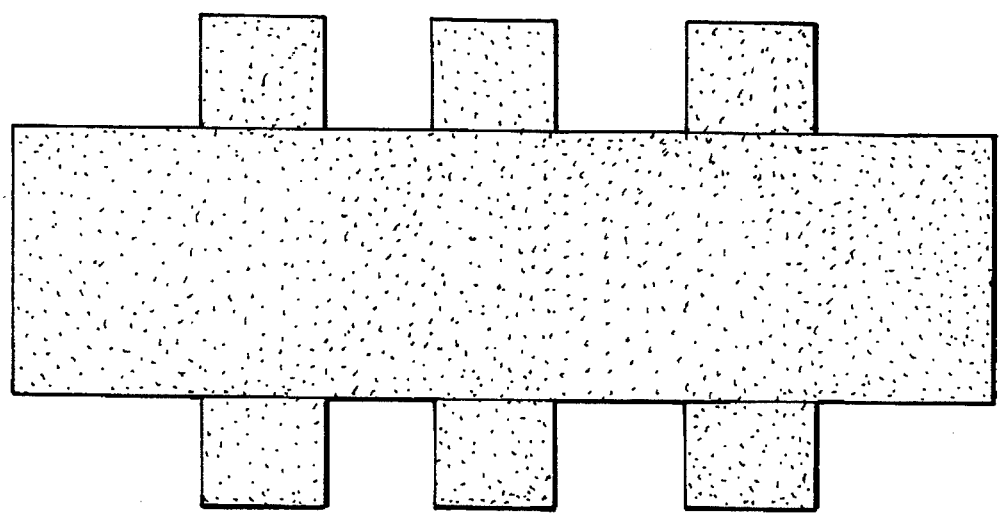
Figure 8A:
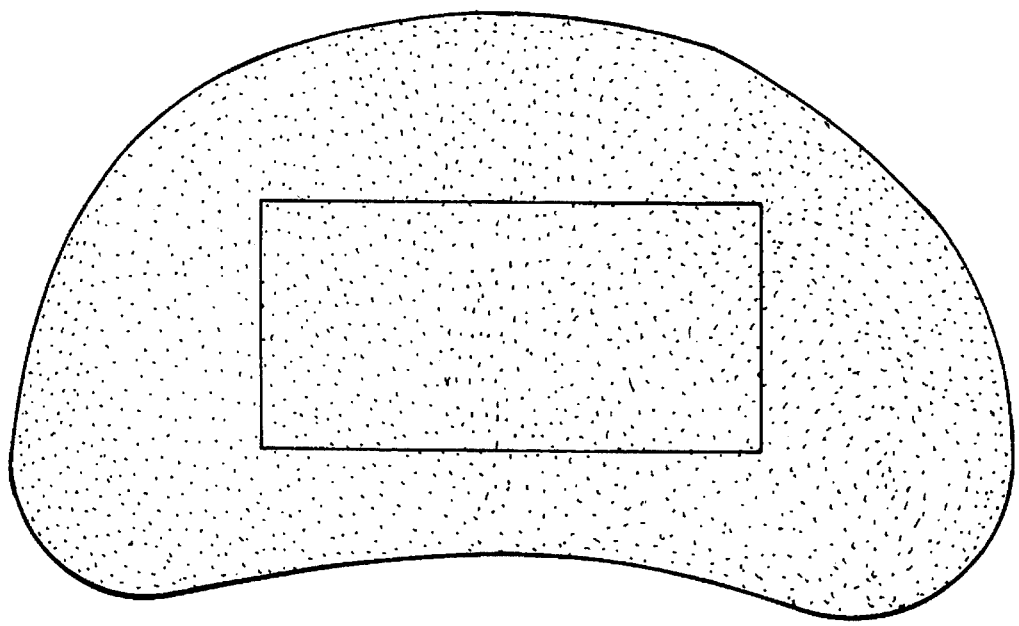
FIG. 8 is a side view in cross-section of a spinal disc spacer with an inclined wedge molded mounted on the outer surfaces of the endplates.
Figure 8B:
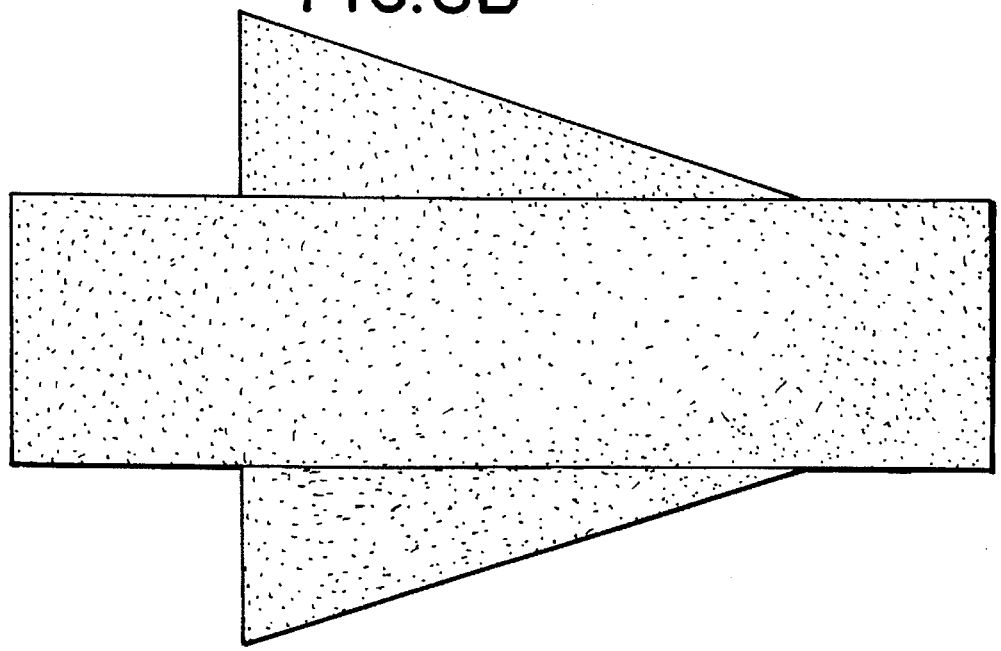
Figure 9:
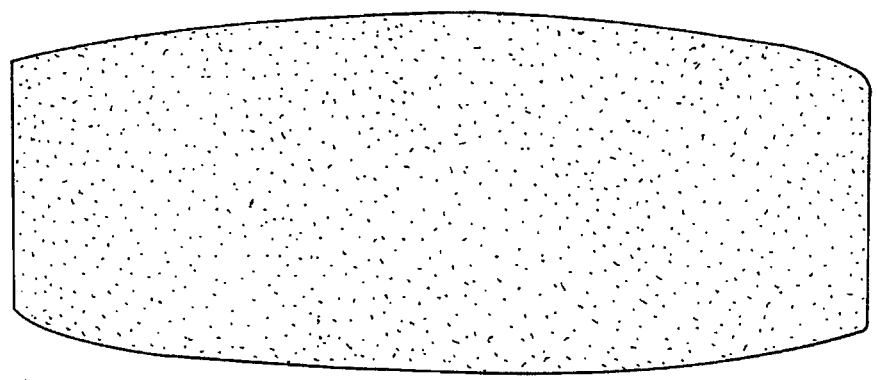
FIG. 9 is a side view in cross-section of a disc spacer with dome-shaped outer surfaces of the endplates.

The three endplate designs which were evaluated are shown in FIGS. 7, 8 and 9. They included the incorporation of three cylindrical pegs, a single inclined plane on both top and bottom surfaces of the implant, and a dome-shaped surface. The pegs were each 2.0 mm in diameter and 2.5 mm high at the raised side. The dome was formed so that the center-was 1.5 mm higher than the lateral edges. Each procedure or design was tested on four segments. The data are presented below in Table IV.

TABLE IV

CANINE SPACER PUSHOUT TEST
ENDPLATE DESIGN EVALUATION

| Trial | Level | Max Force(N) | Initial Slope (N/mm) | F @ .3 mm | Comments/mode of failure |
|---|---|---|---|---|---|
| ORIGINAL SURGICAL PROCEDURE | | | | | |
| 1 | L2–3 | 115.0 | | 17.5 | |
| 2 | L5–6 | 252.5* | | 22.5 | pushed out-ram may have impinged on vertebral bone |
| 3 | L2–3 | 397.5* | | 17.5 | pushed out-ram may have impinged on vertebral bone |
| 4 | L5–6 | 282.5* | | 27.5 | pushed out-ram may have impinged on vertebral bone |
| 5 | L2–3 | 160.0 | 11.6 | 39.0 | |
| 6 | L5–6 | 262.5 | 25.9 | 25.0 | |
| 7 | L2–3 | 132.5 | 25.0 | 16.0 | |
| 8 | L5–6 | 102.5 | 17.5 | 21.0 | |
| Mean | | 154.5 | 20.0 | 23.7 | *not included in mean or standard |
| St Dev | | 64.1 | 6.7 | 9.2 | Deviation |
| OSSEOUS SUTURING | | | | | |
| 9 | L2–3 | 157.5 | 80.0 | 15.0 | suture torn from one vertebrate body |
| 10 | L5–6 | 510.0 | 30.0 | 22.5 | moved to suture @ 145N-disc never pushed out-rotated within defect |
| 11 | L5–6 | 145.0 | 83.8 | 42.5 | moved to suture @ 117.5N, suture broke @ max. |
| 12 | L5–6 | 165.0 | 87.5 | 42.5 | moved to suture @ 140N, suture torn from one vertebral body |
| 13 | L2–3 | 137.5 | 42.5 | 27.5 | moved to suture @ 22.5N, suture torn from one vertebral body @ max. |
| 14 | L5–6 | 297.5 | 42.5 | 35.0 | moved to suture @ 110N, suture broke @ max. |
| Mean | | 235.4 | 61.1 | 30.8 | |
| StDev | | 158.7 | 21.7 | 11.1 | |
| RESORBABLE PINS (POLYSULFONE 3.25 mm DIAMETER | | | | | |
| 15 | L2–3 | 287.5 | 92.5 | 35.0 | disc damaged as pushed through pins |
| 16 | L5–6 | 482.5 | 57.5 | 50.0 | (longer pins) moved to pins at 165N-disc damaged pins bent @ max. |
| 17 | L2–3 | 352.5 | 96.4 | 52.5 | moved to pins @ 117.5-disc damaged Pins bent @ max. |
| 18 | L5–6 | 320.0 | 112.5 | 52.5 | moved to pins @ 120N-disc damaged pins bent @ max |
| Mean | | 360.6 | 89.7 | 47.5 | |
| StDev | | 85.5 | 23.2 | 8.4 | |

TABLE IV-continued

CANINE SPACER PUSHOUT TEST
ENDPLATE DESIGN EVALUATION

| Trial | Level | Max Force(N) | Initial Slope (N/mm) | F @ .3 mm | Comments/mode of failure |
|---|---|---|---|---|---|
| \multicolumn{6}{c}{METAL ENDPLATES} |
| 19 | L2–3 | 450.0* | 147.5 | 30.0 | rate changed from 1N/sec to 100N/sec @ 155N |
| 20 | L5–6 | 300.0 | 117.5 | 57.5 | |
| 21 | L2–3 | 175.0 | 232.1 | 100.0 | |
| 22 | L5–6 | 345.0 | 162.5 | 70.0 | |
| Mean | | 273.3 | 170.7 | 75.8 | *not included in mean |
| StDev | | 88.1 | 57.7 | 21.8 | or standard deviation |
| \multicolumn{6}{c}{DOME-SHAPED ENDPLATES} |
| 23 | L2–3 | + | 35.0 | 50.0 | + Spacer did not dislodge. Actuator ram dug into polymer |
| 24 | L5–6 | + | 115.0 | 102.5 | |
| 25 | L2–3 | + | 37.5 | 52.5 | |
| 26 | L5–6 | + | 45.0 | 55.0 | |
| Mean | | | 58.1 | 65.0 | |
| stDev | | | 38.2 | 25.1 | |
| \multicolumn{6}{c}{POLYMERIC PEGS} |
| 27 | L2–3 | 210.0 | 67.5 | 60.0 | no "toe" in graph-no initial migration |
| 28 | L5–6 | 197.5 | 87.5 | 70.0 | no "toe" in graph-no initial migration |
| 29 | L2–3 | 265.0 | 78.7 | 25.0 | no "toe" in graph-no initial migration |
| 30 | L2–3 | 232.5 | 91.3 | 22.5 | no "toe" in graph-no initial migration |
| 31 | L5–6 | 257.5* | 100* | 17.5* | disc poorly set, actuator impinged on bone (*not included) |
| 32 | L2–3 | 140.0 | 115.0 | 40.0 | |
| 33 | L5–6 | 165.0 | 155.0 | 57.5 | |
| Mean | | 201.71 | 99.2 | 45.8 | |
| StDev | | 45.2 | 31.6 | 19.7 | |
| \multicolumn{6}{c}{POLYMERIC INCLINED WEDGE} |
| 34 | L5–6 | 145.0 | 52.5 | 47.5 | initial slope less than with pegs |
| 35 | L5–6 | 135.0 | 85.0 | 45.0 | |
| 36 | L5–6 | 130.0 | 88.8 | 52.5 | |
| 37 | L2–3 | 175.5 | 77.5 | 42.5 | |
| Mean | | 146.4 | 75.9 | 46.9 | |
| StDev | | 20.4 | 16.3 | 4.3 | |

Endplate Design Evaluation

With the goal of mechanically providing increased initial fixation of the disc spacer into the vertebral bone, six surgical or design modifications were evaluated in terms of their ability to resist shear forces. For comparative purposes, the resistance provided by the flat, HA coated spacer was also tested. The data from all seven sets of tests are summarized in Table V.

TABLE V

Endplate Design Modifications: Resistance to Lateral Shear Forces

| | Initial Slope (N/mm) | Force (N) @ 3 mm Deflection | Maximum Force (N) at Push-Out |
|---|---|---|---|
| Original design and Procedure | 20.0 ± 6.7 | 23. ± 9.2 | 23.7 ± 9.5 4.4 ± 64.1 |
| Osseous Suturing | 61.1 ± 21.7* | 30.8 ± 11.1 | 235.4 ± 158.7 |
| Resorbable Pins | 89.7 ± 23.2* | 47.5 ± 8.4* | 360.6 ± 85.5* |
| Metal Endplates | 170.7 ± 57.6* | 75.8 ± 21.8* | 273.3 ± 88.1* |
| Polymeric Pegs | 99.2 ± 31.6* | 45.8 ± 19.7* | 201.7 ± 45.2 |
| Polymeric wedge | 75.9 ± 16.3* | 46.9 ± 4.3* | 146.4 ± 20.4 |

TABLE V-continued

| | Endplate Design Modifications: Resistance to Lateral Shear Forces | | |
|---|---|---|---|
| | Initial Slope (N/mm) | Force (N) @ 3 mm Deflection | Maximum Force (N) at Push-Out |
| Dome-shaped Endplate | 58.1 ± 38.2* | 65.0 ± 25.1* | ** |

*Significantly greater than original surgical procedure (unpaired).
**Spacer did not dislodge - actuator ram dug into polymer.

Figure 11A:
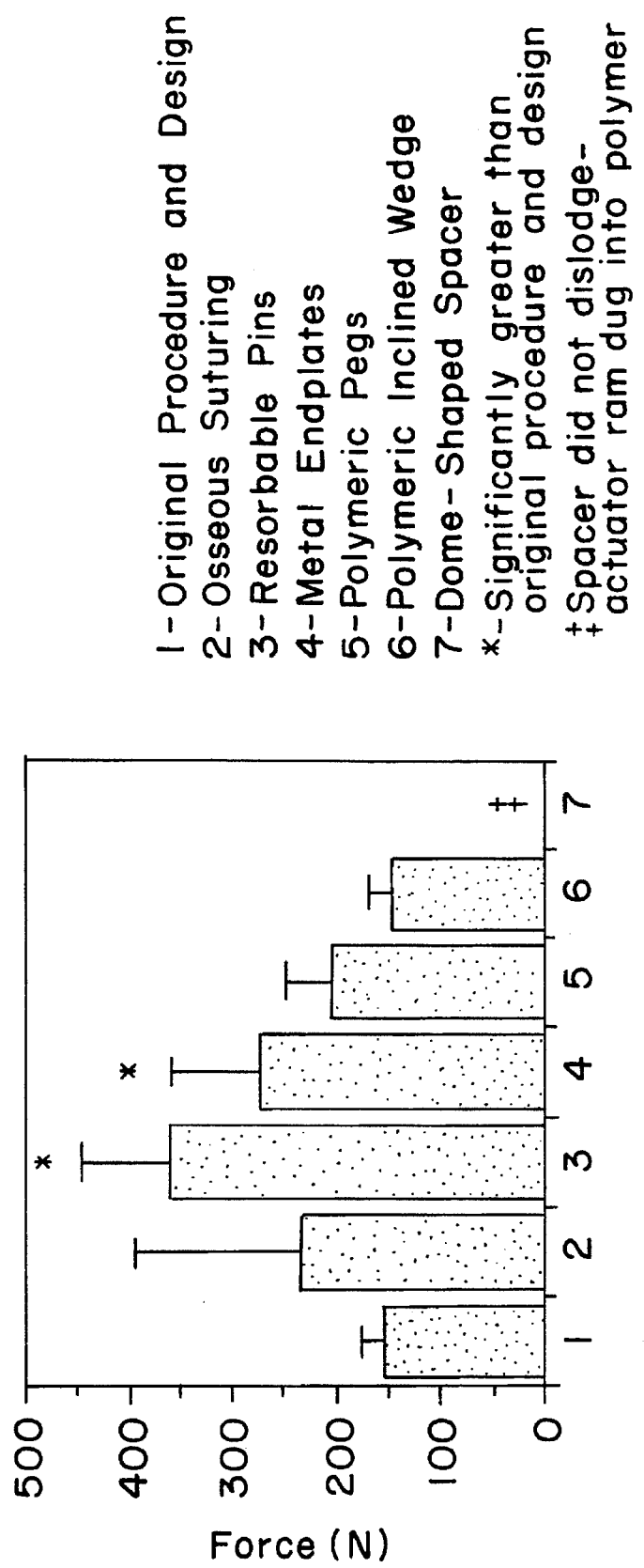
FIG. 11 is a series of graphs showing the compressive force necessary to dislodge prosthetic devices using different endplate designs.
Figure 11C:
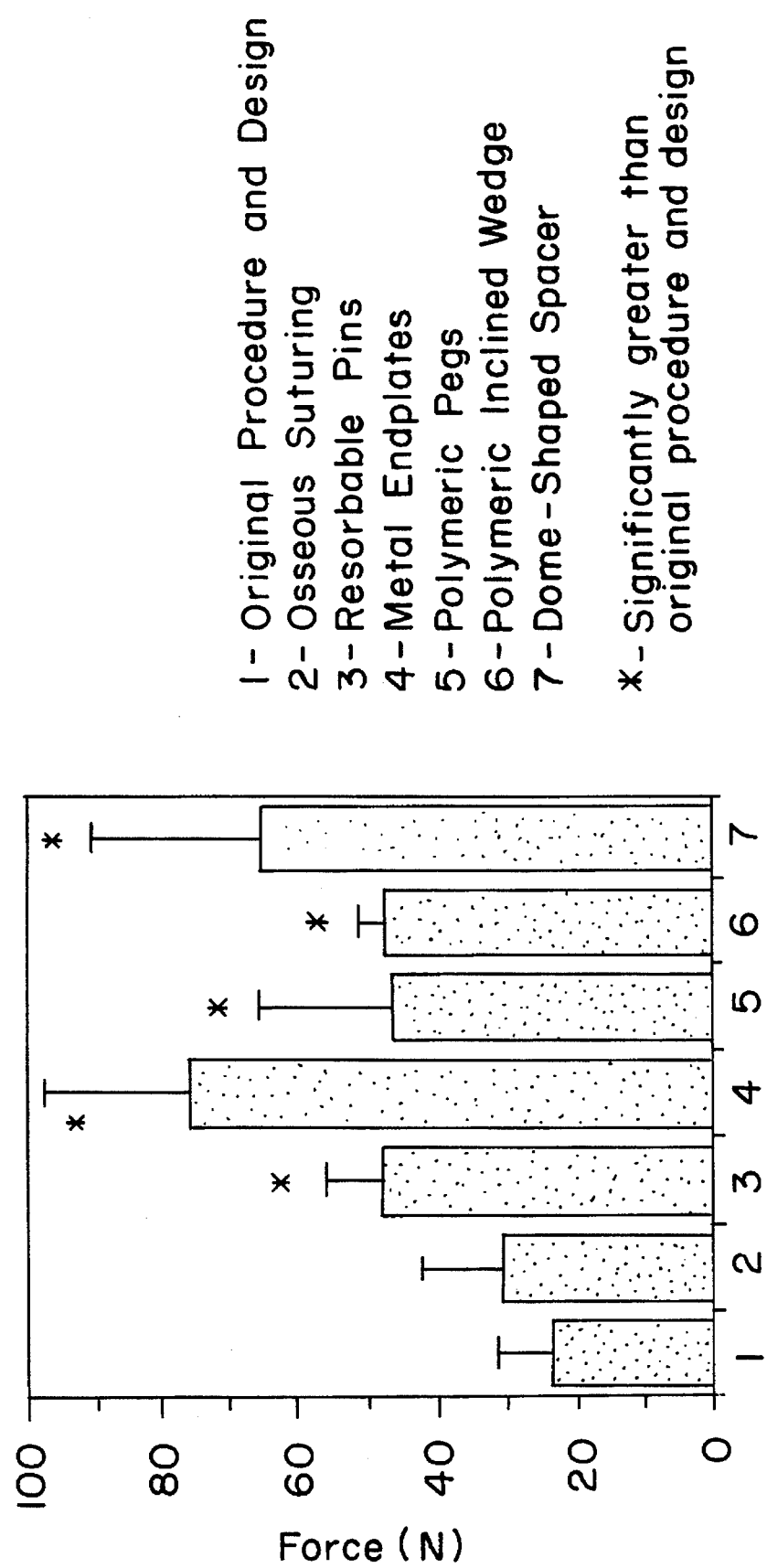

The data are shown graphically in FIGS. 11a–11c. In several tests, the actuator ram was noted to impinge on vertebral bone. The raw data from these tests were not included in mean calculations. All parameters were analyzed for statistical differences from the original design on an unpaired basis.

As can be seen in Tables IV and V and in FIGS. 11a–11c, osseous suturing provided the smallest increase in resistance with only significantly greater initial slope. Molded polymeric interlocking devices (pegs and wedge) performed essentially the same with significantly greater initial resistance (slope and force at three millimeters deflection) than the original procedure. Both resorbable pins and metal endplates provided substantially more resistance as demonstrated by higher results in initial slope, force at three millimeters, and maximum force.

With respect to dome-shaped spacers implanted in a concave surgically prepared bony defect, both initial slope (58.1±38.2N/mm) and force at three millimeters deflection (65.0±25.1N/mm) were significantly greater than the original procedure (20.0±6.7N/mm and 27.1±9.2N/mm). However, it was not possible to evaluate maximum force as, in all cases, the spacer provided so much resistance to lateral movement that the actuator ram actually dug into the implanted polymeric material.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. A biocompatible intervertebral spacer comprising:
    a central core of an unreinforced soft biocompatible elastomeric material shaped and sized so as to approximate the nucleus pulposus of a natural intervertebral disc;
    an outer ring of unreinforced stiffer elastomeric material surrounding said central core to approximate a natural annulus fibrosus, said outer ring and said central core forming a disc having upper and lower surfaces; and
    endplates comprised of a suitably stiff biocompatible material and affixed on one surface with additional elastomeric material, one to each end, to the upper and lower surfaces said endplates having a design modification on their outer surfaces which interdigitates with the adjacent bone;
    said spacer having a mean torsional stiffness of from 0.8 Nm/degree to 3.0 Nm degree and a mean axial stiffness of from 1000 newtons/mm to about 3000 newtons/mm.

2. A spacer according to claim 1 wherein the endplates include metal spikes attached to their outer surfaces.

3. A spacer according to claim 1 wherein the endplates are comprised of elastomeric material.

4. A spacer according to claim 3 wherein the endplates are molded to provide dome-shaped outer surfaces.

5. A spacer according to claim 3 wherein the endplates include polymeric pegs on the outer surfaces.

6. A spacer according to claim 3 wherein the endplates include a polymeric inclined wedge on the outer surfaces.

* * * * *